(12) United States Patent
Saitoh et al.

(10) Patent No.: US 10,004,630 B2
(45) Date of Patent: Jun. 26, 2018

(54) WEARABLE TOILET SEAT

(71) Applicant: Keiko Saitoh, Miyagi (JP)

(72) Inventors: Keiko Saitoh, Miyagi (JP); Tokuo Saitoh, Miyagi (JP)

(73) Assignee: Keiko Saitoh (JP)

( * ) Notice: Subject to any disclaimer, the term of this patent is extended or adjusted under 35 U.S.C. 154(b) by 7 days.

(21) Appl. No.: 15/029,043

(22) PCT Filed: Jan. 19, 2015

(86) PCT No.: PCT/JP2015/000196
§ 371 (c)(1),
(2) Date: Apr. 13, 2016

(87) PCT Pub. No.: WO2015/107908
PCT Pub. Date: Jul. 23, 2015

(65) Prior Publication Data
US 2016/0310313 A1    Oct. 27, 2016

(30) Foreign Application Priority Data

Jan. 20, 2014 (JP) .................................. 2014-008090
Mar. 13, 2014 (JP) .................................. 2014-049883

(51) Int. Cl.
*A61G 9/00* (2006.01)
*A61F 5/451* (2006.01)
*A61F 5/44* (2006.01)

(52) U.S. Cl.
CPC ............... *A61F 5/451* (2013.01); *A61F 5/44* (2013.01); *A61G 9/00* (2013.01)

(58) Field of Classification Search
CPC . C61F 5/451; C61F 5/453; A61G 9/00; A61F 5/451; A61F 5/453
(Continued)

(56) References Cited

U.S. PATENT DOCUMENTS 5,342,583 A * 8/1994 Son .................. A61F 5/451
 2/84
6,554,817 B1 * 4/2003 Oki .................. A61F 5/451
 4/455
(Continued)

FOREIGN PATENT DOCUMENTS

JP    2006-141590    6/2006
JP    2008-142243    6/2008
(Continued)

*Primary Examiner* — Huyen Le
(74) *Attorney, Agent, or Firm* — Jordan and Koda, PLLC

(57) ABSTRACT

A wearable toilet seat includes a back cover portion 11 is fitted at the main body of the toilet seat 10 equipping the defecated fecal receiving portion 14 and the discharged urine receiving portion 15 from the back side and the bottom surface of the main body 10, the rinse solution nozzle 17 equipping the upward spray nozzle 43 and the horizontal spray nozzle 44 and the wind-guide long hole 25 opening upward are arranged as facing the defecated fecal receiving portion 14 in the main body 10, the anterior cover portion 12 is covered on the wind-guide long hole 25 as having a gap in a manner that the air blasting route 46 is on the wind-guide long hole 25, and the assembly ligula 90 of the frontal marginal region of the anterior cover portion 12 is fixed with the assembly ligula 21 of the defecated fecal receiving portion 14 and the assembly ligula 36 of the discharged urine receiving portion 15 at the hip receiving portion 13.

3 Claims, 15 Drawing Sheets

(58) Field of Classification Search
USPC .............................................................. 4/450
See application file for complete search history.

(56) References Cited

U.S. PATENT DOCUMENTS

| | | | | |
|---|---|---|---|---|
| 2008/0178377 | A1* | 7/2008 | Liu | A47K 11/02 |
| | | | | 4/450 |
| 2009/0193572 | A1 | 8/2009 | Nakamura et al. | |
| 2013/0158489 | A1* | 6/2013 | Ying | A61F 5/451 |
| | | | | 604/355 |
| 2015/0328072 | A1 | 11/2015 | Saitoh et al. | |

FOREIGN PATENT DOCUMENTS

| | | |
|---|---|---|
| JP | 2009-183422 | 8/2009 |
| JP | 5254498 | 8/2013 |

* cited by examiner

WEARABLE TOILET SEAT

TECHNICAL FIELD

The present invention relates to a wearable toilet seat for evacuating the bowels in a dorsal position or side lying position on bed etc., used by persons requiring nursing care such as the solitary elderly who cannot urinate/evacuate by oneself or persons with severe conditions who cannot move freely, which enables to reduce the occurrence of bed sore even for its long-term usage or by change in body position and also to prevent urinary leakage as far as possible.

BACKGROUND ART OF THE INVENTION

The inventor et al. of the patent application have already proposed a wearable toilet seat which is worn with the diaper at the groin of a patient at a nursing care facility or a person confined to bed and requiring nursing case for automatically detecting a urination and defecation and then evacuating and processing (Patent literatures 1, 2, and 3).

The wearable seat in the patent literature 1 is as shown in FIG. 19 and the wearable seat in the patent literature 2 is the seat improved from one written. The wearable toilet seat in the patent literature 3 is almost the same as that in the patent literature 1.

In FIG. 19, individual portions are indicated as follows, 100: excretion helping tool, 110: main body, 111: movable connecting portion, 112: rinse-solution supply port, 113: warm-air supply port, 114: excretion port, 115: connecting terminal, 120: anterior cup portion, 130: gluteal supporting portion, 131: cushion layer, 132: hollow portion, 140: opening portion, 200: cover for wearing the excretion helping tool, 201: front body region, 202: inside leg region, 203: back body region, 204: side flap, 206: double-fastener tub, 210: opening portion, 220: top sheet, 230: back sheet, 231: peel-off paper, 240: face-fastener, 250: retentive sheet, 251: face fastener, 252: face fastener, 260: three-dimensional gather, 270: leakage-preventive barrier.

PRIOR ART PATENTS

Patent Literatures

Patent literature 1: JP2008-142243A
Patent literature 2: JP2006-141590A
Patent literature 3: JP5254498B1

The wearable toilet seats shown in the patent literatures 1 and 3 have problems as follows:
(1) The assembly procedures of an excretion helping tool 100 being comprised of many portions are troublesome. Particularly, the configuration to connect from a rinse-solution supply port 112, warm-aft supply port 113, excretion port 114, and connecting terminal 115 at the back surface of a main body 110 to the marginal region and bottom surface of an excretion port 114 through the inside of the main body 110 is so troublesome that leakage of the solution or air inside the main body 110 occurs and its appropriate rinsing effect of excretory substances cannot be obtained.
(2) Because an anterior cup portion 120 is set at the upper portion of the main body 110, the anterior cup portion 120 becomes impeditive in case that a person with a large body wears it and the cup produces an excessive gap under the cup in case that a person with a undersized body wears it, so that the cup couldn't be worn appropriately. Therefore, it was required to prepare some types according to body shapes.
(3) Although a cushion layer 131 is set at a gluteal supporting portion 130, only the diaper is present at the groin and hip region such as the femoral root getting in touch with the main body 110, in which bed sore occurs easily. Particularly, in persons who can conduct body change or bending and stretching of the legs easily, a load is produced locally or graze occurs locally, which facilitates to cause sore bed.
(4) Although any excretory substance excreted to an opening portion 140 is washed down mainly by rinsing solution, because of insufficient wash-down action, a part of the excretory substances remain to cause fetid odor.
(5) Because a suction tube connected to an excretion port 114 is hard, when the body position is changed or the waist is bent as the backrest of the bed is set afoot, the suction tube becomes impeditive.

The object of the present invention is to provide a wearable toilet seat to enable the following achievements:
(1) The assembly is simple, any leakage of air or solution is absent inside the main body, and excretory substances can be washed down appropriately.
(2) Even if body shapes vary in different sexes, any person can wear it appropriately.
(3) Bed sore doesn't occur in change in body position and bending and stretching of the legs.
(4) Any excretory substance can be washed down promptly and cleanly.
(5) As remaining with attached the toilet seat, change in body position or bending of the waist as the backrest of the bad is set afoot is possible.

SUMMARY OF THE INVENTION

The present invention is characterized by that a back cover portion 11 is fitted with a main body of the toilet seat 10 equipping a defecated fecal receiving portion 14 and a discharged urine receiving portion 15 from the back and bottom surfaces of the main body of this toilet seat 10; as facing the defecated fecal receiving portion 14 of the main body of the toilet seat 10, a rinse solution nozzle 17 equipping an upward spray nozzle 43 and a horizontal spray nozzle 44 and a wind-guide long hole 25 opening upward are set, an anterior cover portion 12 is put on with a gap as an air blasting route 46 is present on the wind guide long hole 25; and an assembly ligula 90 of the anterior end of the anterior cover portion 12 is fixed with an assembly ligula 21 of the main body of the toilet seat 10 and an assembly ligula 36 of the back cover portion 11 at a hip receiving portion 13.

The present invention is characterized by comprising the main body of the toilet seat 10 equipping the nearly horizontal bowl-like defecated fecal receiving portion 14 and the nearly vertical canaliform discharged urine receiving portion 15, the back cover portion 11 fitted from the back and bottom surface of the main body of the toilet seat 10 and the hip receiving portion 13 mounted at the anterior end of the main body of the toilet seat 10; in which a bed-sore preventive member is mounted at the marginal region of the defecated fecal receiving portion 14 and the discharged urine receiving portion 15, the upper surface of the hip receiving portion 13 and the bottom surface of the back cover portion 11; the bed-sore preventive member mounted at the marginal region of the defecated fecal receiving portion 14 and the discharged urine receiving portion 15 and the bottom surface of the back cover portion 11 is made from silicon rubber of 5~15 degree in hardness by JISA and the bed-sore preventive member mounted at the upper surface of the hip receiving portion 13 is made from gel member of 4~10 degree in hardness by Asker C.

In addition, a femoral receiving portion 16 formed at the marginal region from the discharged urine receiving portion 15 to the defecated fecal receiving portion 14 is characterized by being formed to become gradually wider toward downward direction.

The present invention is characterized by comprising the main body of the toilet seat 10 equipping the nearly horizontal bowl-like defecated fecal receiving portion 14 and nearly vertical canaliform discharged urine receiving portion 15, a basal airspace portion 29 at the bottom surface of the main body of the toilet seat 10, the fitted back cover portion 11 having a backside airspace portion 30 at the back, and the hip receiving portion 13 mounted at the anterior end of the main body 10; in which as facing the defecated fecal receiving portion 14, the rinse solution nozzle 17, the air blasting route 46, a defecated fecal suction hole 19, a fecal sensor 23 and a urine sensor 24 are equipped; the rinse solution nozzle 18 is equipped as facing the discharged urine receiving portion 15; an air-blasting pipe connecting member 49 and an water pipe connecting member 50 and a connector 51 are equipped at the backside airspace portion 30; and an air-blasting pipe 56 connecting the air-blasting pipe connecting member 49 and the air blasting route 46, the water conduit pipe 45 connecting the water pipe connecting member 50, the rinse solution nozzle 17, and the rinse solution nozzle 18, and an electric cord 55 connecting the connector 51, the fecal sensor 23 and the urine sensor 24 are arranged through the backside airspace portion 30 and the basal airspace portion 29.

The present invention is characterized by comprising the main body of the toilet seat 10 equipping the nearly horizontal bowl-like defecated fecal receiving portion 14 and the nearly vertical caniliform discharged urine receiving portion 15 and the basal airspace portion 29 at the bottom surface of the main body of the toilet seat 10, in which the fitted back cover having the backside airspace portion 30 at the back and a tubular portion 26 becoming the defecated fecal suction hole 19 at the posterior end of the main body of the toilet seat 10 are equipped; a flexing excretory-substance suction hose 52 is connected to the tubular portion 26 placed at a position not to protrude from a hose plug-in hole 32 set at the bottom of the back cover portion 11.

The present invention is characterized by that the back cover portion 11 is fitted at the main body of the toilet seat 10 equipping the defecated fecal receiving portion 14 and the discharged urine receiving portion 15 from the back side and the bottom surface of the main body 10; the wind-guide long hole 25 opening upward is set at the marginal region 91 of the defecated fecal receiving portion 14 in the main body of the toilet seat 10; the anterior cover portion 12 is put on with a gap on the wind-guide long hole 25, a cylinder cowling 39 is set with a gap along the line of an inner wall portion 88 of the defecated fecal receiving portion 14 of the anterior cover portion 12; multiple wind-guide fins 40 are set with a specified interval at positions in a gap with the inner wall portion 88 of the cylinder cowling 39; and the regions among the wind-guide fins 40 are made the air blasting routes 46.

It is also characterized by that the interval and angle of the wind-guide fins 40 are formed in a manger that the wind volume to almost the center in the defecated fecal receiving portion 14 becomes larger than those at both the side in order to facilitate the wash-out of the feces at its use of dorsal position.

According to the invention, because there are the main body of the toilet seat equipping the nearly horizontal bowl-like defecated fecal receiving portion and the nearly vertical caniliform discharged urine receiving portion, the back cover fitted from the back side and the bottom surface of the main body, and the hip receiving portion set at the anterior end of the main body, and the bed-sore preventive member is mounted at the marginal region of the defecated fecal receiving portion and the discharged urine receiving portion and at the upper surface of the hip receiving portion, the bed-sore preventive function in the toilet seat can be configurated easily.

According to the invention, because the bed-sore preventive member is mounted in a manner that the bottom surface of the back cover portion 11 and a part of the bilateral surfaces continuing from said bottom surface are covered, bed sore can be prevented surely even in case of change in body position such as rolling over.

According to the invention, because the bed-sore preventive member mounted at the marginal region of the defecated fecal receiving portion and the discharged urine receiving portion is made from silicon of 5~15 degree in hardness by JISA and the bed-sore preventive member mounted at the upper surface of the hip receiving portion is made from gel member of 4~10 degree in hardness by Asker C, it can be reduced to 50~32 mmHg or less of the body pressure which doesn't cause bed sore when the toilet seat is used with the diaper.

According to the invention, because the femoral receiving portion formed from the marginal region of the discharged urine receiving portion to the marginal region of the defecated fecal receiving portion is formed to become gradually wider toward downward direction, bed sore in the femoral region which moves particularly easily can be prevented.

According to the invention, because there are the main body of the toilet seat equipping the nearly horizontal bowl-like defecated fecal receiving portion and the nearly vertical caniliform discharged urine receiving portion, the basal airspace portion at the bottom surface of the defecated fecal receiving portion in the main body, the fated back cover portion 11 having the backside airspace portion at the back of the discharged urine receiving portion, and the hip receiving portion set at the anterior end of said main body; and pipes sending water and wind are arranged at said defecated fecal receiving portion and said discharged urine receiving portion through said backside airspace portion and the basal airspace portion, the resistances at sending water and wind can be reduced without leakage, which results in better efficient cleansing.

According to the invention, because the rinse-solution nozzle, air blasting route, defecated fecal suction hole, fecal sensor, and urine sensor are equipped as facing the defecated fecal receiving portion; the rinse solution nozzle is equipped as facing the discharged urine receiving portion; the blast pipe connecting member, water pipe connecting member, and connector are set at the backside airspace portion of the back cover; the air-blasting, pipe connecting said air blasting duet connecting member and air blasting route, the water pipe connecting said water pipe connecting member and rinse-solution nozzle and rinse solution nozzle, and the electric cord connecting said connector and fecal sensor and urine sensor are arranged through said backside airspace portion to the basal airspace portion, the parts can be assembled easily and the maintenance can be done effectively.

According to the invention, because the back cover is fitted at the main body of the toilet seat equipping the defecated fecal receiving portion and the discharged urine receiving portion from the bask side and the bottom surface of said main body; the wind-guide long hole opening upward at the marginal region of the defecated fecal receiving portion in said main body; the anterior cover portion 12 is put on with a gap on the wind-guide long hole; the cylinder cowling is set with a gap along the line of the inner wall of the defecated fecal receiving portion of the anterior cover portion; multiple wind-guide fins are set with a designated interval at a position in the gap with the inner wall of the cylinder cowling; and the regions among these wind-guide fins are made the air blasting routes, the wind volumes at the center and both the sides in the defecated fecal receiving portion can be set in accordance with purpose such dorsal position or side lying position etc. by adjusting the angles and intervals of the multiple wind-guide fins.

According to the invention, because the intervals and angles of the wind-guide fins are formed in a manner that the wind volume to the nearly center of the defecated fecal receiving portion becomes larger than those at both the sides, it is appropriate to use the toilet seat at dorsal position.

According to the invention, because the intervals and angles of the wind-guide fins are formed in such a manner that the wind volume to both the sides of the defecated fecal receiving portion becomes larger than that at the center, it is appropriate to use the toilet seat at side lying position.

DETAILED DESCRIPTION OF THE PREFERRED EMBODIMENTS

Figure 1:
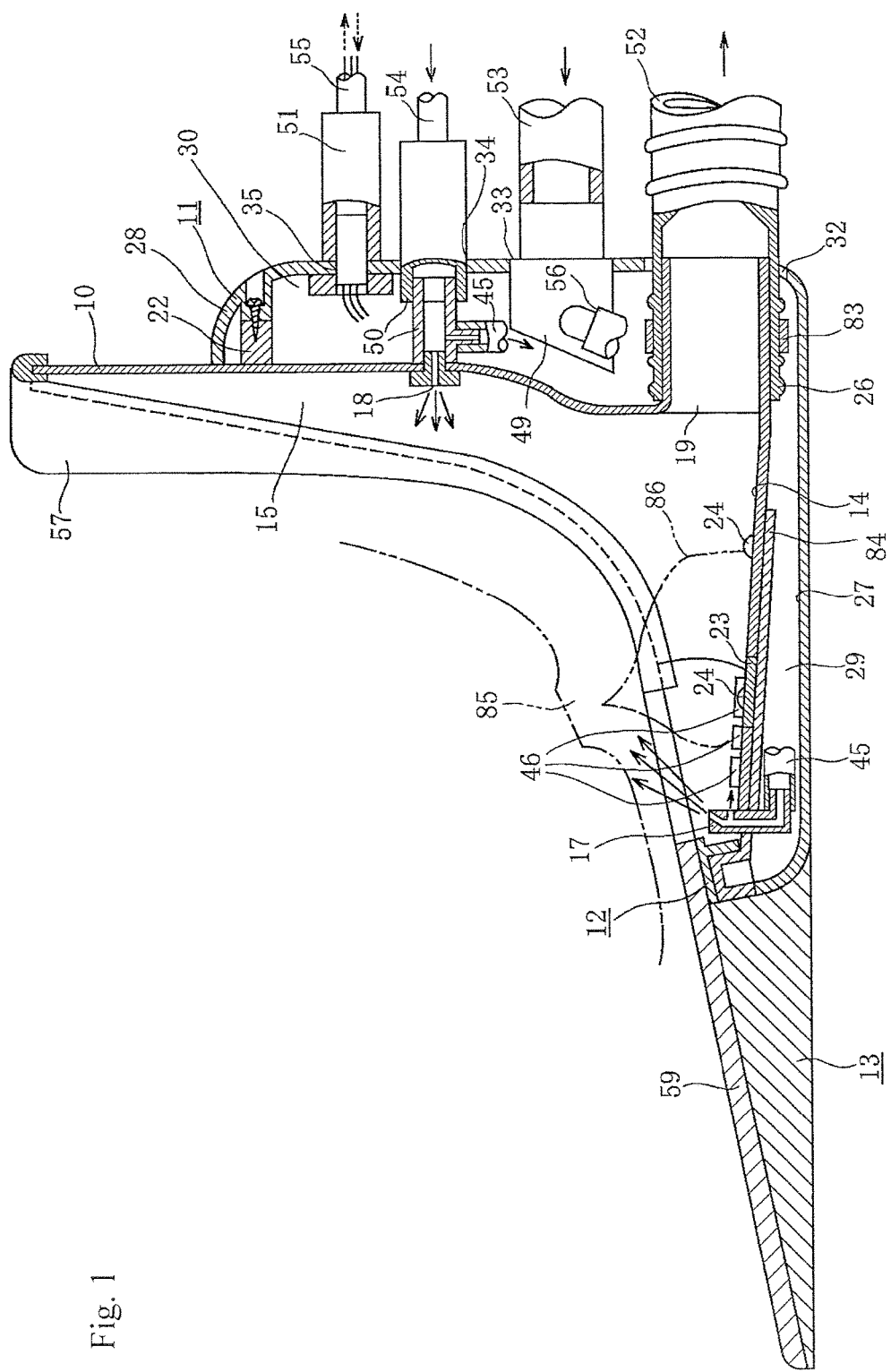
FIG. 1 is a longitudinal viewing surface showing a case of embodiment of the wearable toilet seat relating to the present invention.

The present invention facilitates to assemble the defecated fecal receiving portion 14 and the discharged urine receiving portion 15 at the hip receiving portion 13 easily and surely in an integral manner by the following procedures: The back cover portion 11 is fitted at the main body of the wearable toilet seat 10 equipping the defecated fecal receiving portion 14 and the discharged urine receiving portion 15 from the back side and the bottom surface of said main body 10, the assembly ligulas 21 and 36 set at the anterior ends of the said main body 10 and the back cover portion 11 are overlapped and then put in the plug-in groove 61 of the hip receiving portion 13 for fixation.

The invention enables to assemble the air blasting mechanism only by mounting the anterior cover portion 12 at the same time when the defecated fecal receiving portion 14 and the discharged urine receiving portion 15 are mounted at the hip receiving portion 13 by means of the following procedures: The rinse solution nozzle 17 equipping the upward spray nozzle 43 and the horizontal spray nozzle 44 and the wind-guide long hole 25 opening upward are set as facing the defecated fecal receiving portion 14 in said main body 10, the anterior cover portion 12 is covered with a gap as the air blasting route 46 is present on the wind-guide long hole 25, and the assembly ligula 90 of the anterior end of the anterior cover portion 12 is fixed with individual assembly ligulas 21 and 36 of said main body 10 of the toilet seat and the back cover portion 11 at the hip receiving portion 13. In addition, because the conventional anterior cup at the upper end is absent, an appropriate gas is produced for persons with large or small body, which enables to wear it appropriately. Thus, it is unnecessary to prepare some types according to the body shapes.

The present invention, comprising the main body 10 of the wearable toilet seat 10 equipping the nearly horizontal bowl-like defecated fecal receiving portion 14 and the nearly vertical caniliform discharged urine receiving portion 15, the back cover portion 11 fitted from the back side and bottom surface of said main body, and the hip receiving portion 13 set at the anterior end of said main body 10, enables to easily configure the bed-sore preventive function in the toilet seat by mounting the bed-sore preventive members 57, 58, and 59 at the marginal regions 91 and 92 of said defecated fecal receiving portion 14 and said discharged urine receiving portion 15 and at the upper surface of said hip receiving portion 13.

The invention enables to surely prevent bed sore by mounting the bed-sore preventive member 93 as the bottom surface in the back cover portion 11 and a part of both the sides continuing from said bottom surface are covered even in case of change in body position such as rolling over.

The invention enables to decrease the body pressure to 50~32 mmHg or less which doesn't cause bed sore when the diaper is used as an interposition, because the bed-sore-preventive member mounted at the marginal regions of the defecated fecal receiving portion and the discharged urine receiving portion and at the bottom surface of the back cover portion 11 is made from silicon of 5~15 degree in hardness by JISA and the bed-sore preventive member mounted at the upper surface of the hip receiving portion is made from gel member of 4~10 degree in hardness by Asker C.

The invention enables to prevent bed sore at the thigh which is especially movable by means of forming the femoral receiving portion 16 formed from the marginal region 92 of the discharged urine receiving portion 15 to the marginal region 91 of the defecated fecal receiving portion 14 in a manner to become gradually wider in downward direction.

The prevention, comprising the main body of the wearable toilet set 10 equipping the nearly horizontal bowl-like defecated fecal receiving portion 14 and the nearly vertical caniliform discharged urine receiving portion 15, the basal airspace portion 29 at the bottom surface of the defecated fecal receiving portion 14 in said main body 10, the fitted back cover portion 11 having the backside airspace portion 28 at the back of the discharged urine receiving portion 15, and the hip receiving portion 13 set at the anterior end in said main body 10, enables to decrease the resistance without leakage at the time of sending water and wind and to conduct the cleansing efficiently by mean of arranging the pipes for sending water and wind at said defecated fecal receiving portion 14 and said discharged urine receiving portion 15 through said backside airspace portion 28 and said basal airspace portion 29.

The present invention, equipping the rinse solution nozzle 17, the air blasting route 46, the defecated fecal suction hole 19, the fecal sensor 23 and the urine sensor 24 as facing the defecated fecal receiving portion 14; the rinse solution nozzle 18 as facing the discharged urine receiving portion 15; the air-blasting pipe connecting member 49 and the water pipe connecting member 50 and the connector 51 at the position of the backside airspace portion 30 of the back cover portion 11; and arranging the air-blasting pipe 66 communicated with said blast pipe 49 and the air blasting route 46, the water conduit pipe 45 communicated with said water pipe connecting member 50, the rinse solution nozzle 17, and the rinse solution nozzle 18, and the electric cord 55 communicated with said connector 51, the fecal sensor 23, and the urine sensor 24 through said backside airspace portion 30 and the basal airspace portion 29, facilitates the assembly of the parts and effective maintenance.

The invention, comprising the main body of the wearable toilet seat 10 equipping the nearly horizontal bowl-like defecated fecal receiving portion 14 and the nearly vertical caniliform discharged urine receiving portion 15, and the basal airspace portion 29 at the bottom surface in said main body 10; and arranging the fitted back cover portion 11 having the backside airspace portion 30 at the back side and the tubular portion becoming the defecated fecal suction hole 19 at the posterior end in the main body 10 with the tubular portion connected to the flexuous excretory-substance suction hose 52, enables a cared person wearing the toilet seat to easily stand up from the waist level and thus facilitates the nursing care.

In the present invention, the tubular tip is placed at a position where the tip doesn't protrude from the hose plug-in hole 32 set at the bottom end of the back cover portion 11, that doesn't disturb when standing up, because its bending occurs soon from the back side of said main body 10.

The invention, treating the nearly horizontal bowl-like defecated fecal receiving portion 14 with coating of low-friction member such as Teflon (registered brand) on the surface, enables to prevent attachment of feces and urine at the defecation and urination and to smoothly flow the excretory substances.

The invention, that in the main body of the toilet seat 10 equipping the defecated fecal receiving portion 14 and the discharged urine receiving portion 15, the back cover portion 11 is fitted from the back side and the bottom surface of said main body 10, the wind-guide long hole 25 opening upward is set at the marginal region 91 of the defected fecal receiving portion 14 in said main body 10, the anterior cover portion 12 is covered with a gap on the wind-guide long hole 25, the cylinder cowling 39 is set with a gap along the line of the inner wall of the defecated fecal receiving portion 14 of the anterior cover portion 12, multiple wind-guide fins 40 are set with a specified interval at positions in the gap with the inner wall of the cylinder cowling 39, and the region among the wind-guide fins 40 are made the air blasting route 46, enables to set wind volumes at the central part and both the sides in the defecated fecal receiving portion 14 according to purpose such as dorsal position or side lysing position etc, by means of adjusting the angles and intervals of multiple wind-guide fins 40.

The invention, that the intervals and angles of the wind-guide fins 40 are formed in a manner that the wind volume to the nearly center in the defecated fecal receiving portion 14 becomes larger than those at both the sides, makes suitable for using it in a condition of dorsal position.

The invention, that the intervals and angles of the wind-guide fins 40 are formed in a manner that the wind volumes to both the sides of the defecated fecal receiving portion 14 becomes larger than that at the center, makes suitable for using it in a condition of side lying position.

Figure 2:
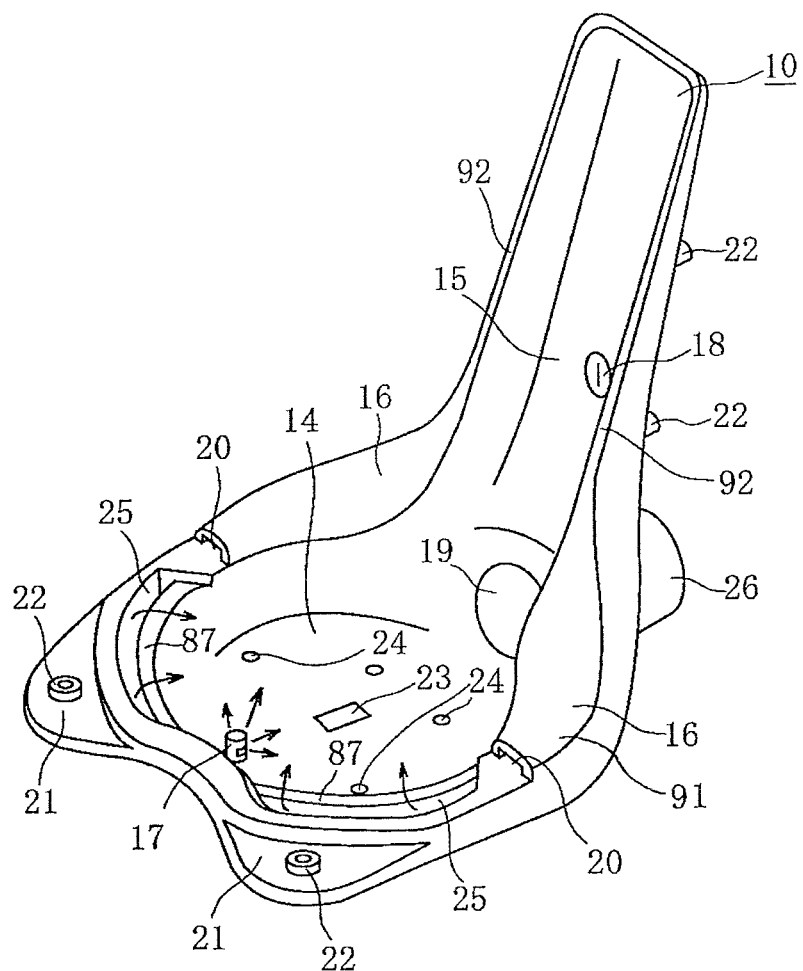
FIG. 2 is a diagrammatic perspective view of the main body of the wearable toilet seat 10 shown in FIG. 1.
Figure 3:
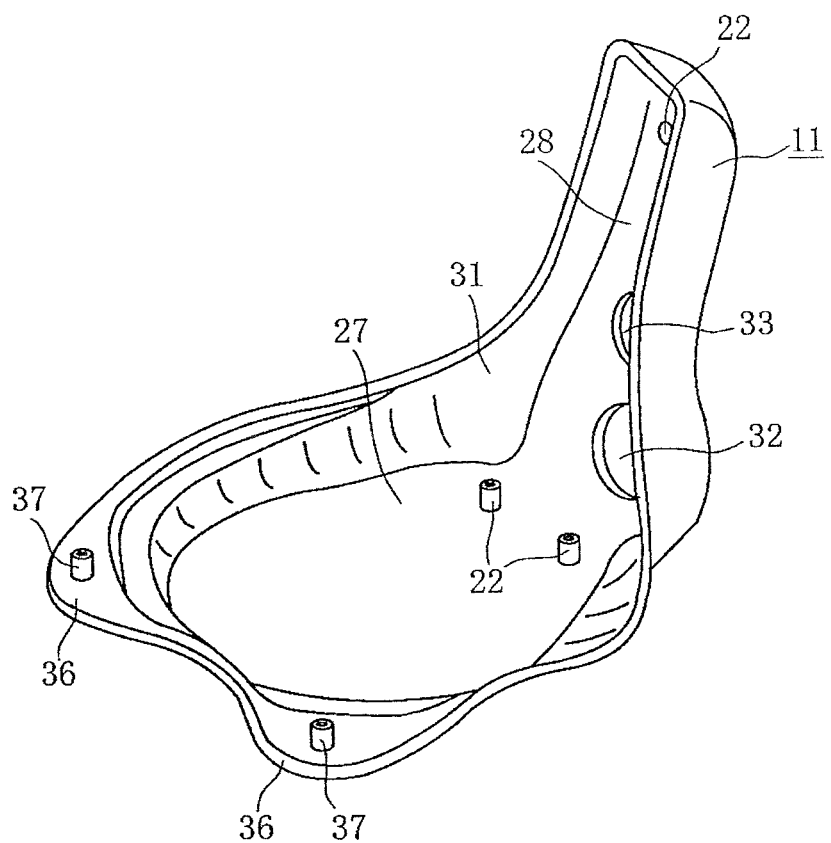
FIG. 3 is a diagrammatic perspective view of the back cover portion 11 shown in FIG. 1.
Figure 7:
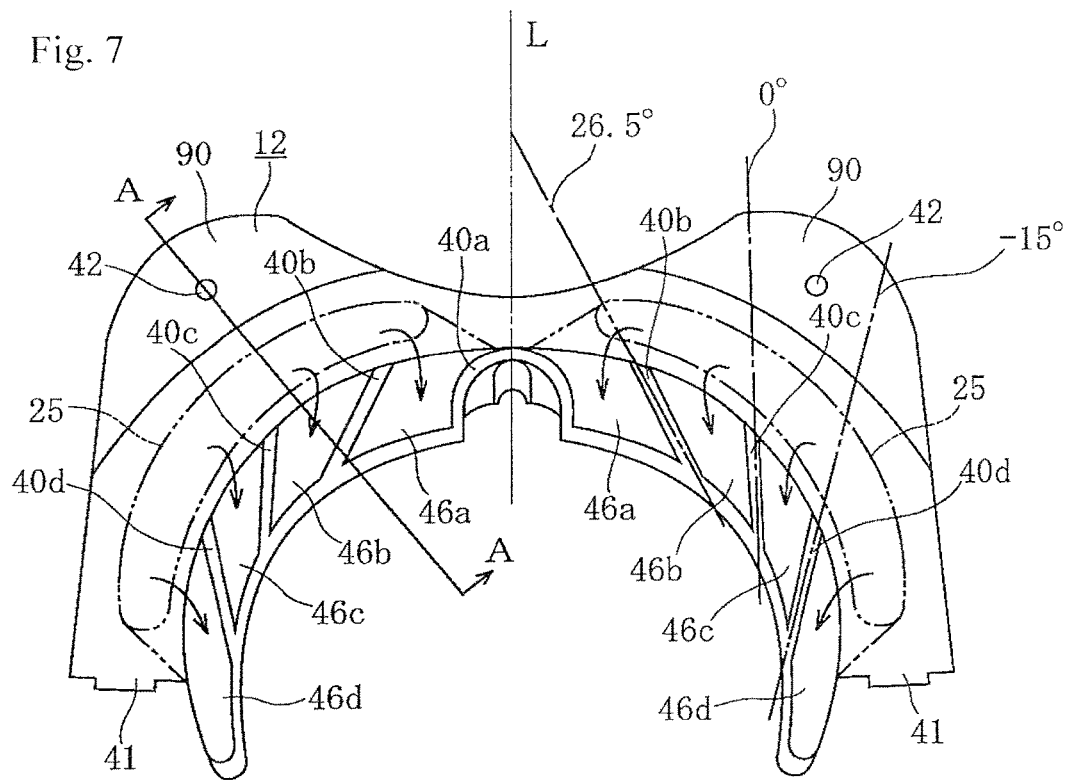
FIG. 7 is a base view of the anterior cover portion 12.
Figure 9:
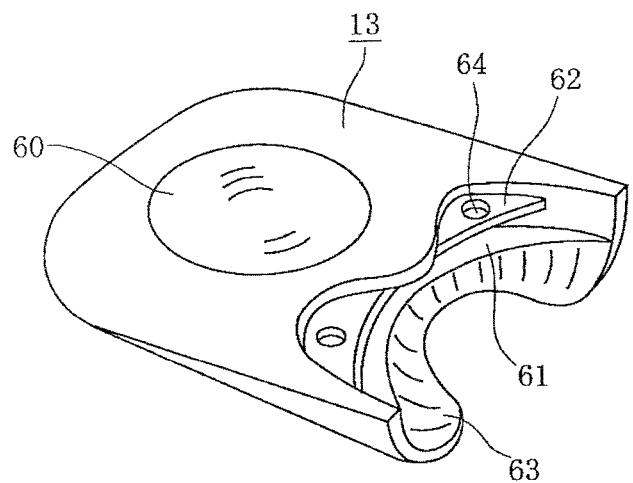
FIG. 9 is a diagrammatic perspective view of the hip receiving portion 13 in FIG. 1.

The present invention of the wearable toilet seat comprises roughly the main body of the toilet seat 10 shown in FIG. 2, the back cover portion 11 shown in FIG. 3, the anterior cover portion 12 shown in FIG. 7, and the hip receiving portion 13 shown in FIG. 9 in a broad way.

Said main body 10, as shown in FIG. 2, comprises the defecated fecal receiving portion 14 having a bowl-like depressed portion of about 100 mm in diameter and the longitudinal caniliform discharged urine receiving portion 15 which tilts at a right angle to the defecated fecal receiving portion 14 or slightly backward to the right angle and is about 50 mm in width, about 170 in height and about 20 mm in depth.

Said defecated fecal receiving portion 14 tilts slightly toward the posterior end from the anterior end and the tubular portion 26 becoming the defecated fecal suction hole 19 in communication with the posterior end projects in a united manner. The defecated fecal receiving portion 14 equips the rinse solution nozzle 17 which sprays warm water to main cleanse the anus 85 and wash out the feces 86 on the upper surface of the defecated fecal receiving portion 14. At the left and right marginal regions 91 of said defecated fecal receiving portion 14, the arcwise wind-guide long holes 25 open respectively and a step 87 is set to flow air at the side of the defecated fecal receiving portion 14 of the wind-guide long hole 25. The wide femoral receiving portion 16 of about 20~30 mm in width is formed in a region from the tip portion of said wind-guide long hole 25 to the marginal region 92 of said discharged urine receiving portion 15 with slight inclination at both the sides. Two assembly ligulas 21 projecting forward from said wind-guide long hole 25 and the assembly projection 22 protrudes at the nearly center. As shown in FIG. 1, a circuit board 84 is set at the back surface of the defeated fecal receiving portion 14, and one fecal sensor 23 mounted at the circuit board is exposed to the nearly center at the upper surface of the defecated fecal receiving portion 14 and four urine sensors 24 are exposed around the fecal sensor 23.

Figure 8:
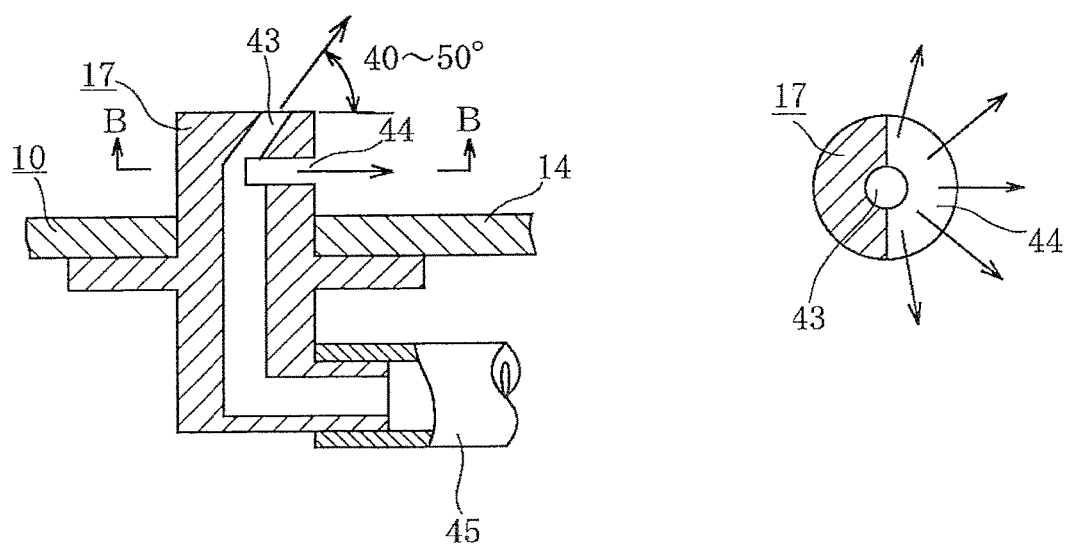
FIG. 8 (*a*) is a longitudinal view of the rinse solution nozzle 17 and (*b*) is a cross-section view of B-B line in (*a*).

The upward spray nozzle 43 cleansing the anus and pubes is equipped with an angle of 40~50 degree to the horizontal level at the upper end of said rinse solution nozzle 17, as shown in FIG. 8(*a*). At the side surface, as shown in FIG. 8 (*b*), the wide horizontal spray nozzle 44 of about 180 degree in angle is set as spraying whole upper surface of the defecated fecal receiving portion 14. At the bottom end of the rinse solution nozzle 17, the water conduit pipe 45 is connected.

As shown in FIG. 2, the rinse solution nozzle 18 to cleanse the anus and pubes is equipped at almost middle position of the discharged urine receiving portion 15. At the back side of the defecated fecal receiving portion 14 and the discharged urine receiving portion 15 in said main body 10, the assembly projections 22 connecting to the back cover portion 11 are made at several positions.

The surface of said defecated fecal receiving portion 14 is coated by low friction member such as Teflon (registered brand name), which prevents the attachment of feces and urine and facilitates to flow smoothly.

As shown in FIG. 3, the back cover portion 11 has a shape similar to said main body of the toilet seat 10 by the basal receiving portion 27, the backside receiving portion 28 and the side wall portion 31. When the back cover is mounted from the back surface of the defecated fecal receiving portion 14 and the discharged urine receiving portion 15 in said main body 10, as shown in FIG. 1, the basal airspace portion 29 are formed at the basal side and both the sides between the defecated fecal receiving portion 14 and the basal receiving portion 27 and the backside airspace portion 30 is formed between the discharged urine receiving portion 15 and the backside receiving portion 28. As shown in FIG. 1, the backside receiving portion 28 of the back cover portion 11 has opening holes of the hose plug-in hole 32, air-blasting pipe mounting hole 33, the rinse solution pipe mounting hole 34, and the connector mounting hole 35 in the order from the bottom.

The assembly projection 22 is made at a position corresponding to the assembly projection 22 in said main body 10 of the basal receiving portion 27 and the backside receiving portion 28. The assembly ligula 36 having the assembly projection 37 at the left and right of the anterior end is equipped.

The flexuous excretory-substance suction hose 52 which isn't crushed is fitted in the tubular portion 26 in the main body of the toilet seat 10 and fixed by joint band 83, and projects from the hose plug-in hole 32 of said back cover portion 11; which facilitates a person wearing the wearable toilet seat to bend over and stand up as remaining in the condition with the toilet seat.

Figure 4:
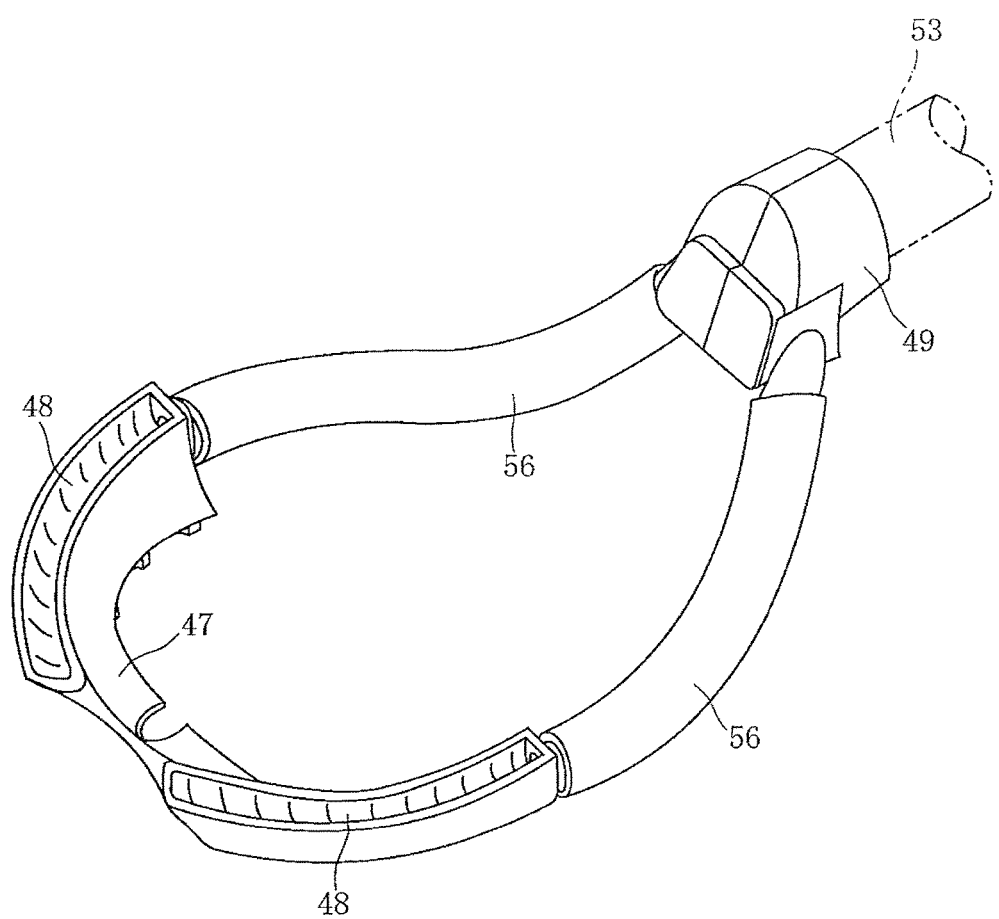
FIG. 4 is a diagrammatic perspective view of the air-supply mechanism.

In the air-blasting pipe mounting hole 33 of said back cover portion 11, the air-blasting pipe connecting member 49 is mounted and the outer air-supply pipe 53 is connected. As shown in FIG. 4, two air-blasting pipes 56 are mounted inside it. In the rinse-solution pipe mounting hole 34, the water pipe connecting member 50 which is connected to the outer warm water pipe 54 and connected to the rinse solution nozzle 18 and the water conduit pipe 45 inside it is mounted.

Said rinse solution nozzle 18 is mounted at the nearly center of the discharged urine receiving portion 15 in an exposed condition and cleanses male and female sexual organs after urination. In the connector mounting hole 35 of said back cover portion 11, the connector 51 having the electric cord 55 is mounted and conducts input/output of electric signals and supply of electric source etc.

Said air-blasting pipe connecting member 49 and the water pipe connecting member 50 and the connector 51 can be mounted in a fixed condition at the backside receiving portion 28 of the back cover portion 11 or can be mounted in a removable condition by connector mechanism which has been known publicly.

In said air-blasting pipe connecting member 49, as shown in FIG. 4, the bifurcated air-blasting pipes 56 are connected and those are connected respectively to wind guide groove members 47, each of which has a circular arc opening of a wind-guide groove portion 48 at the upper surface. Said air-blasting pipe 56 is mounted closely at the bottom surface of said wind-guide long hole 25 through the backside airspace portion 30 formed between the main body 10 and the backside cover portion 11 and the bilateral basal airspace portions 29. As for said air-blasting pipe 56, thicker one as far as possible is used to reduce the resistance at the air blasting and improves the blast power.

The water conduit pipe 45 connected to said water pipe connecting member 50 is connected to the bottom end of said rinse solution nozzle 17 through the backside airspace portion 30 formed between the main body 10 and the back cover portion 11 to the basal airspace portion 29, as shown in FIG. 1. In the rinse solution nozzle 17, the upward spray nozzle 43 mainly cleansing the anus 85 by spraying warm water upward at the angle of about 40~50 degree as shown in FIG. 8 (*a*) and the horizontal spray nozzle 44 cleansing the defecated fecal receiving portion 14 by spraying the rinse solution in fan-like fashion of 180 degree and almost horizontally as shown in FIG. 8 (*b*) are mounted.

The circuit board 84 in which the fecal sensor 23 and the urine sensor 24 are mounted from the back side of the defecated fecal receiving portion 14 of said main body 10 is fixed. Said fecal sensor 23 is exposed at the upper surface of the nearly central portion of the defecated fecal receiving portion 14 and said four urine sensors 24 are mounted around the fecal sensor 23 in an exposed condition at the front.

Figure 5:
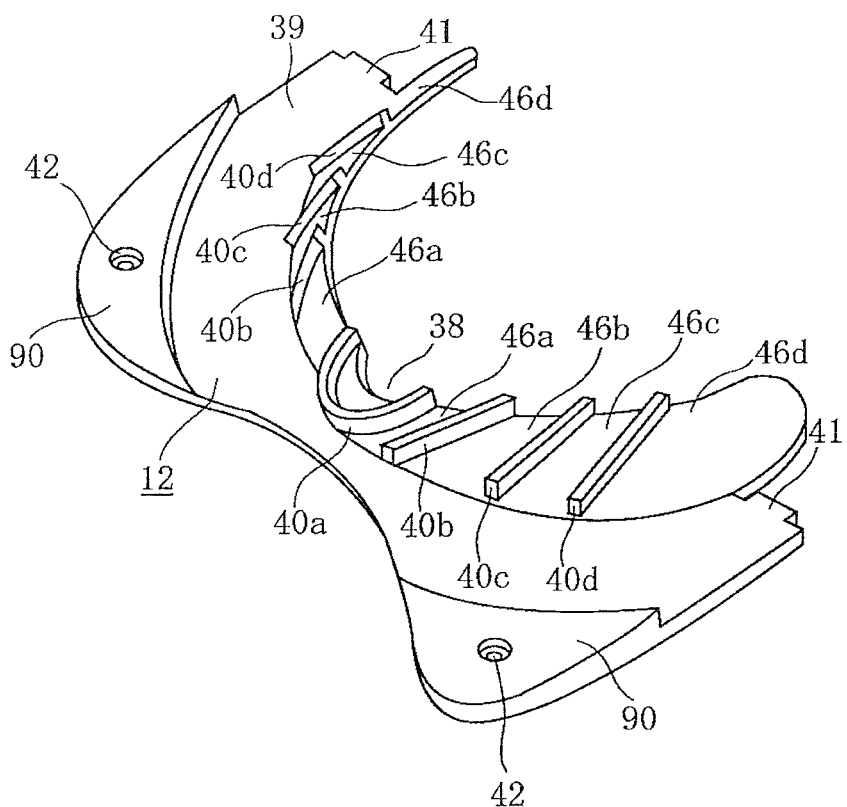
FIG. 5 is a diagrammatic perspective view seen from the back surface of the anterior cover portion 12 shown in FIG. 1.

Tenons 41 of the bilateral tips of the front cover portion 12 is put on the wind-guide long hole 25 of said main body 10 as inletting. Then, in the front cover portion 12, as shown in FIG. 5 and FIG. 7, a U-letter shape wind-guide fin 40*a* is mounted at the center of the back surface, and three wind guide fins 40*b*, 40*c* and 40*d* each are mounted at both the sides of the U-letter shape wind-guide fin 40*a* to configure air blasting routes 46*a*, 46*b* 46*c* and 45*d*, which communicate with the upper surface of the defecated fecal receiving portion 14 for blasting air through a bump 87 of said wind-guide groove portion 48 and the wind-guide long hole 25.

Although the air flow volume from said air blasting routes 46*a*, 46*b*, 46*c* and 46*d* are different according to mutual intervals and angles among the wind-guide fins 40*a*, 40*b*, 40*c* and 40*d*, it was confirmed that the fecal/urine wash-out processing capability is the most efficient when the flow volume of the left and right air blasting routes 46*b*, 46*c* and 46*d* are adjusted to be 30% respectively with about 40% of the two air blasting routes 46*a* at the center.

Specifically, in the center where the initial purpose was achieved in a condition that the wind-guide fin 40*b* extends over 26.5 degree to the central line L, the wind guide fine 40*c* is at zero degree (parallel) to the central line L, and the wind-guide fin 40*d* tilts toward the minus 15 degree to the central line L, a nozzle-escape concave portion 38 is formed.

Figure 6:
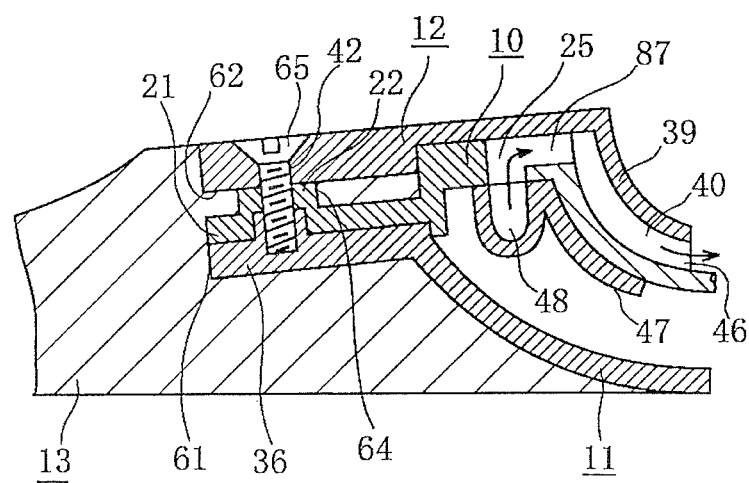
FIG. 6 is a cross-section view of A-A line in FIG. 7.
Figure 10:
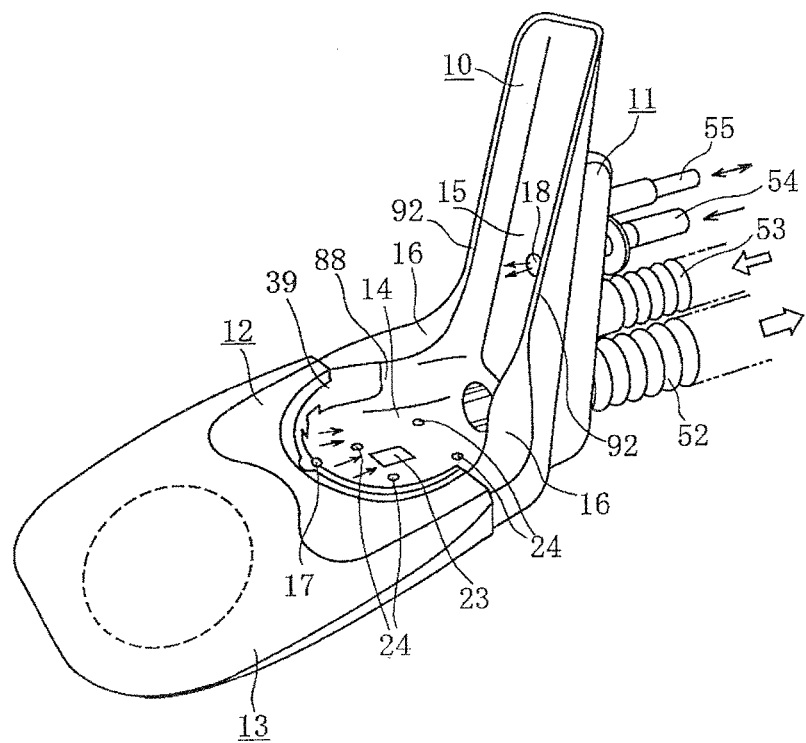
FIG. 10 is a case of embodiment of the wearable toilet seat relating to the invention in the assembled condition of the parts.

The excretory-substance suction hose 52, air-supply pipe 53, water pipe 54, and electric cord 55 are mounted at said back cover portion 11. The circuit board 84 and the wind guide groove member 47 etc. are fixed at the defected fecal receiving portion 14 of the main body of the toilet seat 10 and the back cover portion 11 is fitted in from the bottom surface of the main body 10. Then, the main body 10 and back cover portion 11 are fixed by multiple assembly projections 22 and screws. The assembly ligula 21 of the main body 10 and the assembly ligula 36 of the back cover portion 11 are pressed-fit in the plug-in groove 61 of the hip receiving portion 13 made from elastic body as shown in FIG. 6 in a condition that the assembly projection 37 is fitted in each assembly projection 22 and as shown in FIG. 6, the assembly projection 22 is fitted in the screw hole 64 to unify them. At that time, the bottom portion 63 of the hip receiving portion 13 attaches firmly to the bottom portion of said back cover portion 11. Because the hip receiving portion 13 is made from elastic body, when the assembly ligula 21 and assembly ligula 36 are pressed fit in the plug-in groove 61 which is widened, the assembly projection 22 is fitted in the screw hole 64 to unify them. As described above, after the main body 10 and the back cover portion 11 are fitted in the plug-in groove 61 of the hip receiving portion 13, the tenon 41 of the anterior cover portion 12 is inserted into the tenon hole 20 on the main body 10, and is gotten on the wind-guide long hole 25, and is pillowed on the assembly ligula 90 of the anterior cover portion 12 and then the concave portion 62. After the anterior cover portion 12 is covered, when the screw 65 is screwed into the screw hole 64 of the anterior cover portion 12, the main body 10 and back cover portion 11 and anterior cover portion 12 are fixed together with the hip receiving portion 13 to complete the assembly, as shown in FIG. 10.

Figure 11:
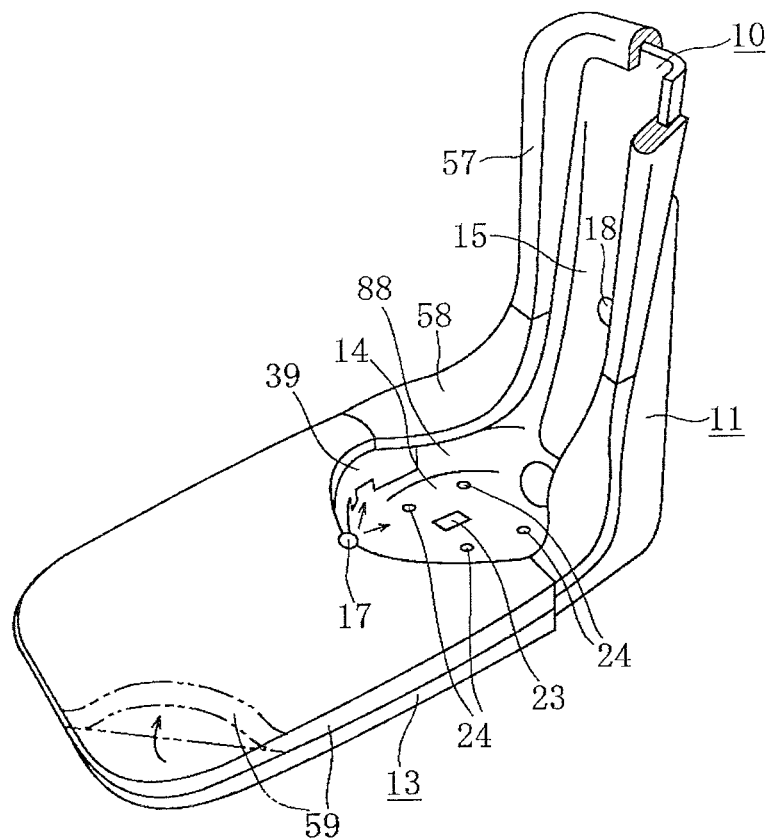
FIG. 11 is a diagrammatic perspective view in a partially notched condition that the bed-sore preventive members is mounted at the wearable toilet seat shown in FIG. 10.

Next, as shown in FIG. 11, the first bed-sore preventive member 57 and second bed-sore preventive member 58 and third bed-sore preventive member 59 are fitted in portions where the skins are compressed at the wearing. Said first bed-sore preventive member 57 is covered on the bilateral marginal regions 92 of the urine receiving portion 15 from the upside. Said second bed-sore preventive member 58 is covered on the femoral receiving portion 16 from the upside. As for the first bed-sore preventive member 57 and second bed-sore preventive member 58, both the members combined body is usable.

When the first bed-sore preventive member 57, second bed-sore preventive member 58, and third bed-sore preventive member 59 are worn with the diaper, it is said desirable that the body pressure is 50 mmHg or less, more preferably 32 mmHg or less.

To meet the condition, said first bed-sore preventive member 57 and the second bed-sore preventive member 58 are made from silicon rubber of 5~15 degree in hardness by JISA and are adhered in a fixed manner. The third bed-sore preventive member 59 mounted at the upper surface of the hip receiving portion 13 is made from gel member of 4~10 degree in hardness by Asker C and it is desirable to be adhesive for easy peeling off and cleaning when any waste matter invades a portion between the hip receiving portion 13 and the third bed-sore preventive member 59. In addition, because the sacral bone comes in contact with the third bed-sore preventive member 59, it is desirable to form the sacral escape concave portion 60 at the hip receiving portion 13 and put the third bed-sore preventive member 59 on it.

Figure 12:
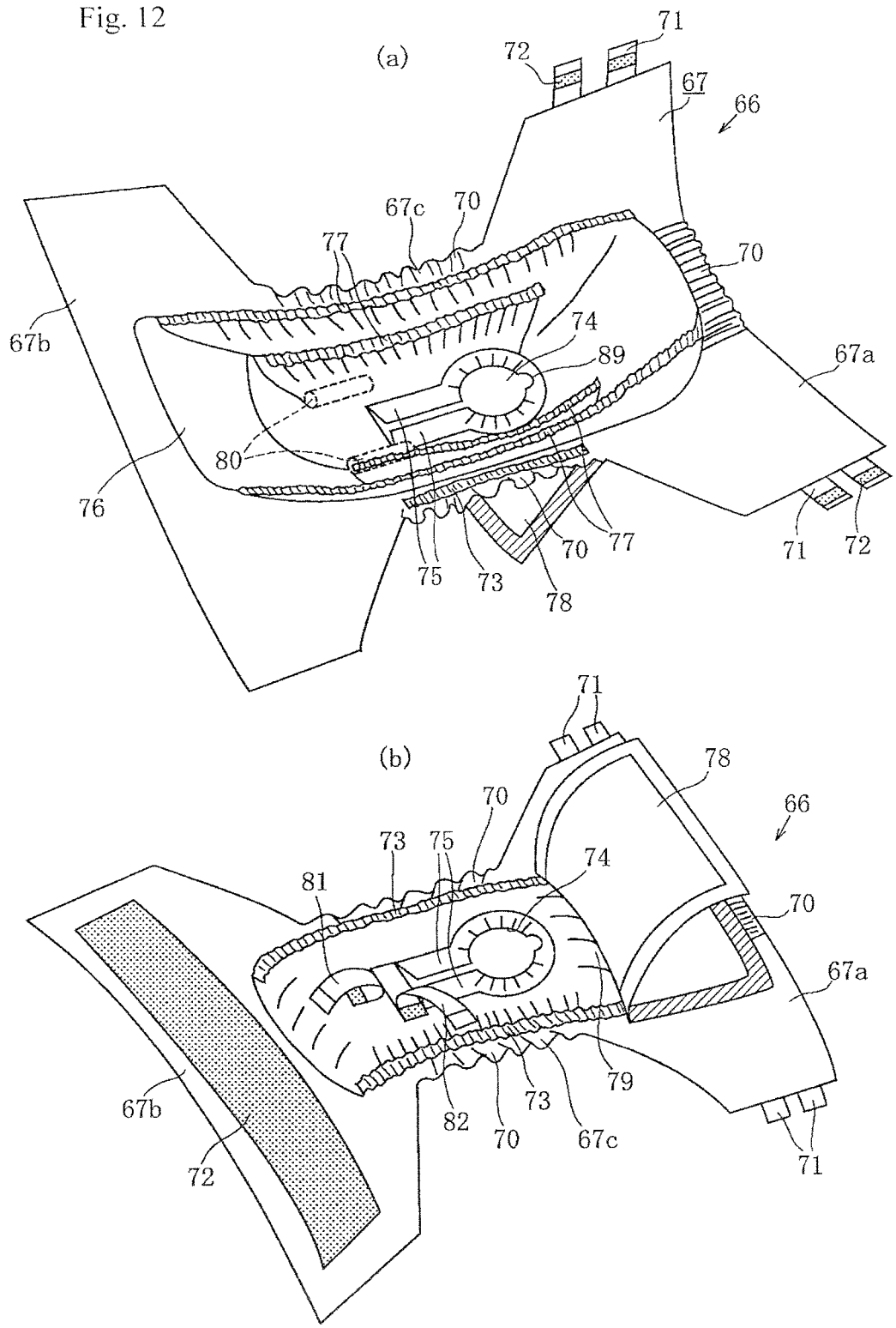
FIG. 12 (*a*) is a diagrammatic perspective view seen from the inner surface of a diaper 66 used for the wearable toilet seat of the invention. (*b*) is a diagrammatic perspective view from the outer surface of (*a*).
Figure 13:
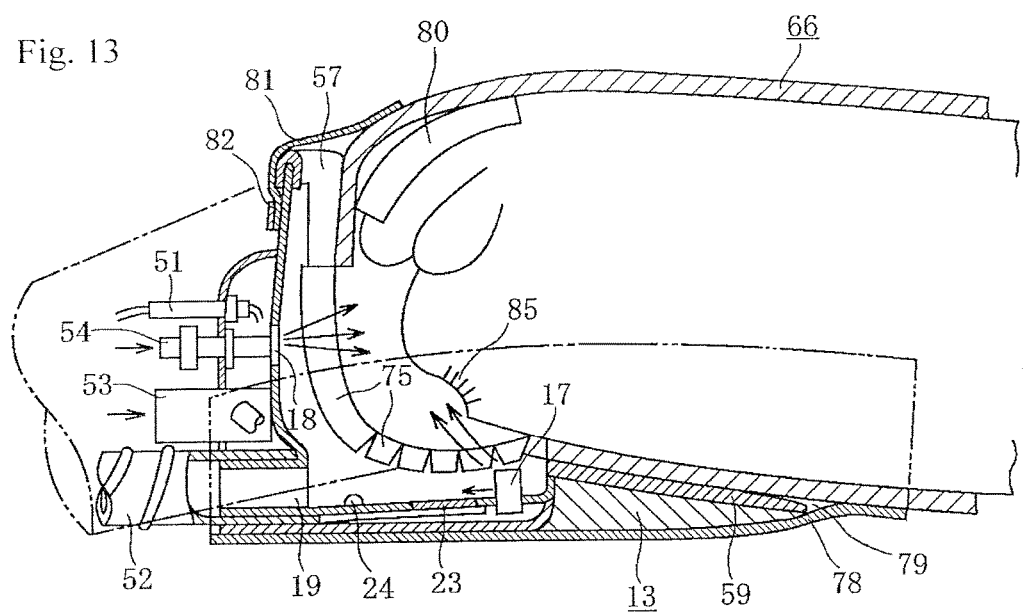
FIG. 13 is a cross-section view in a condition that a person wears the wearable toilet seat with the diaper 66.

The wearable toilet seat configured as explained above is worn between the legs with the diaper 66 as shown in FIGS. 12 (*a*) and (*b*).

An example of the diaper 66 is explained below.

As shown in FIGS. 12 (*a*) and (*b*), the diaper main body 67 comprises a relatively thin sheet consisting of a waist wrapping portion 67*a*, a abdominal contour wrapping portion 67*b*, and a crotch contour wrapping portion 67*c* being narrower than those 67 *a* and *b* and a rectangular cushion member 76 is attached to the inside of the diaper main body 67. An elastic gather 70 is formed at both the sides of said crotch contour wrapping portion 67*c* and the nearly center of the end of said waist contour wrapping portion 67*a*, and a leakage preventive wimple 73 is formed at the bottom surface.

A bottle-guard shape excretion hole 74 is cut out through the cushion member 76 and the crotch contour wrapping portion 67*c*. In an adhesive member 75 inside the circular hole and liner cut of the excretion hole 74, an adhesive layer having a peel-off sheet on the back surface is formed and is fixed with adhesion at the cylinder cowling 39 of the anterior cover portion 12 as shown in FIG. 11 and the inner wall portion 88 of the main body 10.

Two pieces each of a gather tape 77 are fixed at both the sides of the excretion hole 74 and two male sexual organ retentive portion 80 which bulges out in a tubular manner along the line of the mounting region of the inner gather tape 77 are set with a certain interval.

A hygroscopic toilet-seat cover cloth 78 covers a region from the end of the waist contour wrapping portion 67*a* to the excretion hole 74 in the outer surface of said diaper 66. The surrounding other than the region wrapping the excretion hole 74 of the toilet-seat cover cloth 78 is bonded at the bottom surface of the waist contour wrapping portion 67*a* and a portion where the toilet-seat cover cloth 78 and the waist contour wrapping portion 67*a* overlaps becomes a plug-in gap 79. In the peripheral region wrapping the excretion hole 74 of said toilet-seat cover cloth 78, an adhesive layer with a peel-off sheet is formed. In addition, the male sexual organ retentive portion 80 is set at the inner side of the abdominal contour wrapping portion 67*b* side near said excretion hole 74, and an end of a gap retentive tape 81 adheres to the outer side, and an adhesive layer with a peel-off sheet is formed at the other end of the gap retentive tape 81. A fixing member 71 having a face fastener 72 is set at both the sides of said waist contour wrapping portion 67*a* and is combined with a face fastener of the abdominal contour wrapping portion 67*b* in a freely removable manner.

Procedures of wearing the wearable toilet seat configured as described above are explained below.

(1) The hip receiving portion 13 of the toilet seat shown in FIG. 11 is inserted into a point where the tip of the plug-in gap 79 of the diaper 66 shown in FIG. 12 bumps into the inside of the plug-in gap 79. At the point, the excretion hole 74 of the diaper 66 and the defecated fecal receiving portion 14 get together. At that time, the rinse solution nozzle 17 is exposed from a plunger helix 89 of the evaluation hole 74. In this condition, the peel-off sheet of the adhesive member 75 at the peripheral region of the circular hole of the excretion hole 74 is peeled off and pasted at the cylinder cowling 39 of the anterior cover portion 12. The peel-off sheet of the adhesive member 75 of the straight line portion of the excretion hole 74 is peeled off and is bonded at the inner wall portion 88 of the defecated fecal receiving portion 14 and the inner wall of the discharged urine receiving portion 15.

(2) The wearable toilet seat with the diaper 66 gotten on is applied to the crotch in a patient etc. At that time, when the gluteal region of the patient etc. is put on the third bed-sore preventive member 59 in the hip receiving portion 13, a position of the anus is right above the fecal sensor 23 in the defecated fecal receiving portion 14 and the femoral root region attached firmly to the femoral receiving portion 16 in the wearable toilet seat.

(3) When the firm attachment is made, the abdominal contour wrapping portion 67b is folded back up to the abdomen of the patient etc. At that time, in case of male patient etc., the male sexual organ is placed at a gap with the male sexual organ retentive portion 80 and the urinary tract is placed appropriately in a direction toward the discharged urine receiving portion 15. The female sexual organ is faced off against the rinse solution nozzle 18 in the discharged urine receiving portion 15.

(4) The abdominal contour wrapping portion 67b is wrapped round from the upside of the abdomen in the patient etc. and the waist contour wrapping portion 67a is covered as the gather 70 is extended from both the sides of the abdominal contour wrapping portion 67b, and then, the face fastener 72 of the fixing member 71 is latched together with the face fastener 72 of the abdominal contour wrapping portion 67b.

(5) To form an appropriate space between the defecated fecal receiving portion 14 and the discharged urine receiving portion 15 in the wearable toilet seat and the urinary organ in the patients etc. to prevent the attachment of feces and urine to the diaper 66 around the excretion hole 74, the gap retentive tape 81 is pulled in to firmly attach the outer surface of the diaper 66 to the first bed-sore preventive member 57 of the wearable toilet seat, the peel-off sheet is removed from the gap retentive tape 81 to attach it to the back cover portion 11, and moreover, the gap retentive tape 82 is attached to prevent for the gap retentive tape 81 to be peeled off as intersecting with the gap retentive tape 81. In the diaper 66, because two pieces each of the face fastener 72 are formed at both the sides of the excretion hole 74 and the gather 70 is formed at both the sides of the crotch contour wrapping portion 67c, it hardly occur that feces, urine or rinse solution leaks from the diaper 66.

(6) To prevent those to leak from both the sides of the defecated fecal receiving portion 14 and the discharged urine receiving portion 15 because the setting way of the diaper 66 or the wearable toilet seat is insufficient, the outer side of the defecated fecal receiving portion 14 is wrapped by the toilet seat cover cloth 78 outside the diaper 66 and the adhesive sheet of the excretion hole 74 is removed and is bonded at the main body 10 and the back cover portion 11, having no space between them. The toilet seat cover cloth 78 can prevent surely the external leakage from the toilet seat by means of the water-proof and water absorption functions.

As described above, when the wearable toilet seat is worn with the diaper and the fecal sensor 23 or/and the urine sensor 24 detect it/them, the excretory substance processing device which isn't shown in a diagram drives and sucks in the feces or/and urine and processes it, cleanse with warm water and dry by warm wind.

In said embodiment example, as shown in FIG. 7, on the premise of that the wearable toilet seat is worn at the portion between the legs and the defecation and urination is conducted in a dorsal position, anterior cover portion 12 of the wind-guide fins 40a, 40b, 40c and 40d are set in a manner that the wind volume at the central portion becomes 40% and those at the left and right become 30%, respectively.

Figure 14:
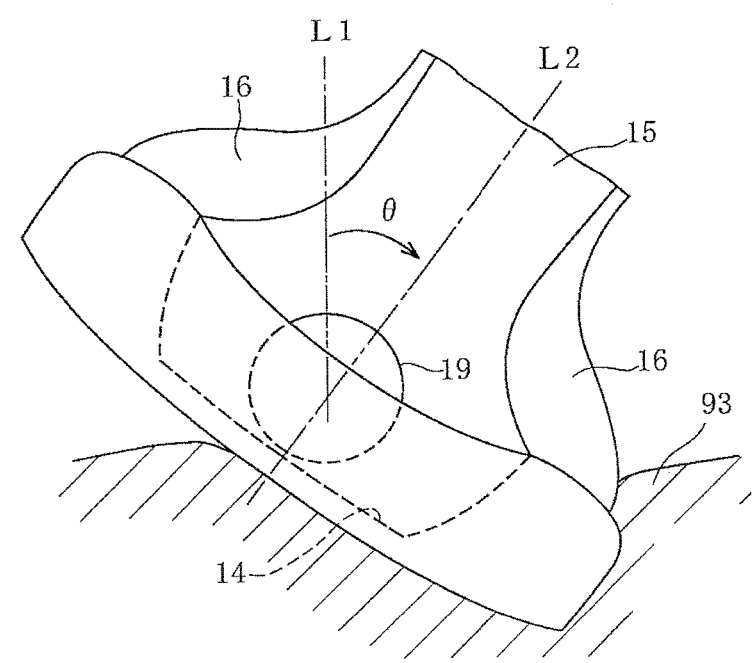
FIG. 14 is a front view in a condition that a person m side lying position wears the wearable toilet seat.
Figure 15:
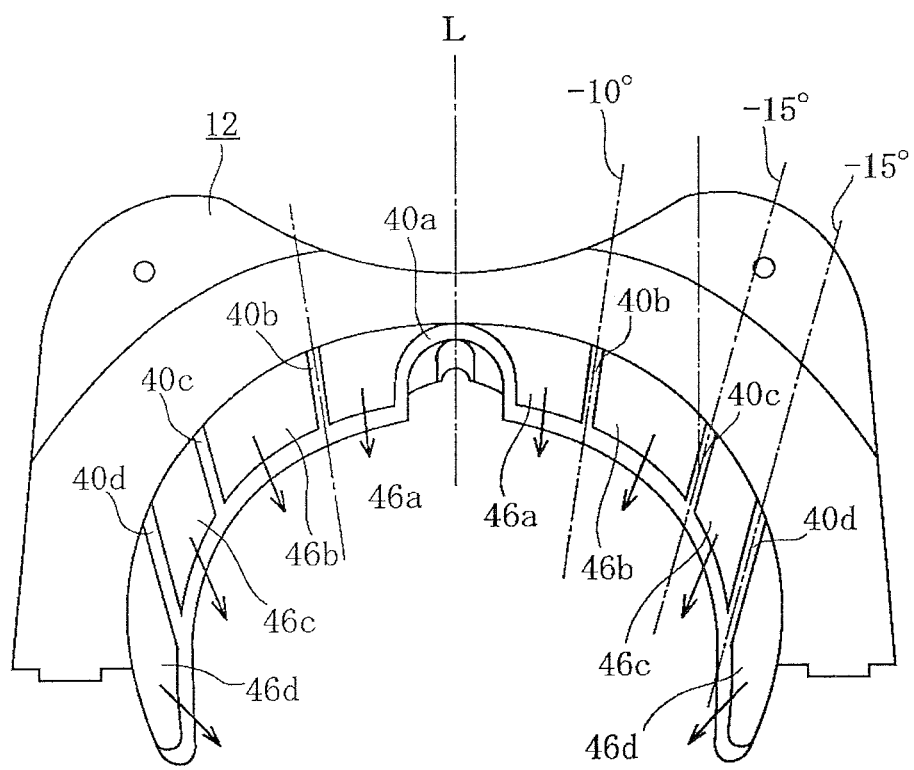
FIG. 15 is a base view showing other case of the wind-guide fins 40 of the anterior cover portion 12 used in case of FIG. 14.

However, as shown in FIG. 14, some persons defecate and urinate in a side lying position as the line L2 which tilts toward only θ from the central line L1. In such cases, as shown in FIG. 15, the angles of the wind-guide fins 40a, 40b, 40c and 40d of the anterior cover portion 12 can be set in a manner that the wind volume at the central portion becomes 30% and those at the left and right becomes 35%, respectively, being higher in the wind volume at the left and right than that at the central portion. In this manner with higher wind volume at the left and right portions, it is effective for the person in a left or right side lying position as change in body position.

For persons in one-side lying position, for example only left side lying position, only the angle of the left fin is formed as shown in FIG. 15 and the right fin can be made the angle in a dorsal position as shown in FIG. 7. In case of right-lying position, it becomes reverse.

In addition, to facilitate side-lying position and change in body position, as shown in FIG. 14, the bottom surface of the back cover portion 11 is made round to facilitate a bed-sore preventive member 93 to dig into.

In said embodiment case, as shown in FIG. 11, the first bed-sore preventive member 57 is covered on the marginal regions 92 of both the sides of the discharged urine receiving portion 15 from the upside, and said second bed-sore preventive member 58 is covered on the femoral receiving portion 16, and the third bed-sore preventive member 59 is covered on the sacral escape concave portion 60 of the hip receiving portion 13.

Figure 16:
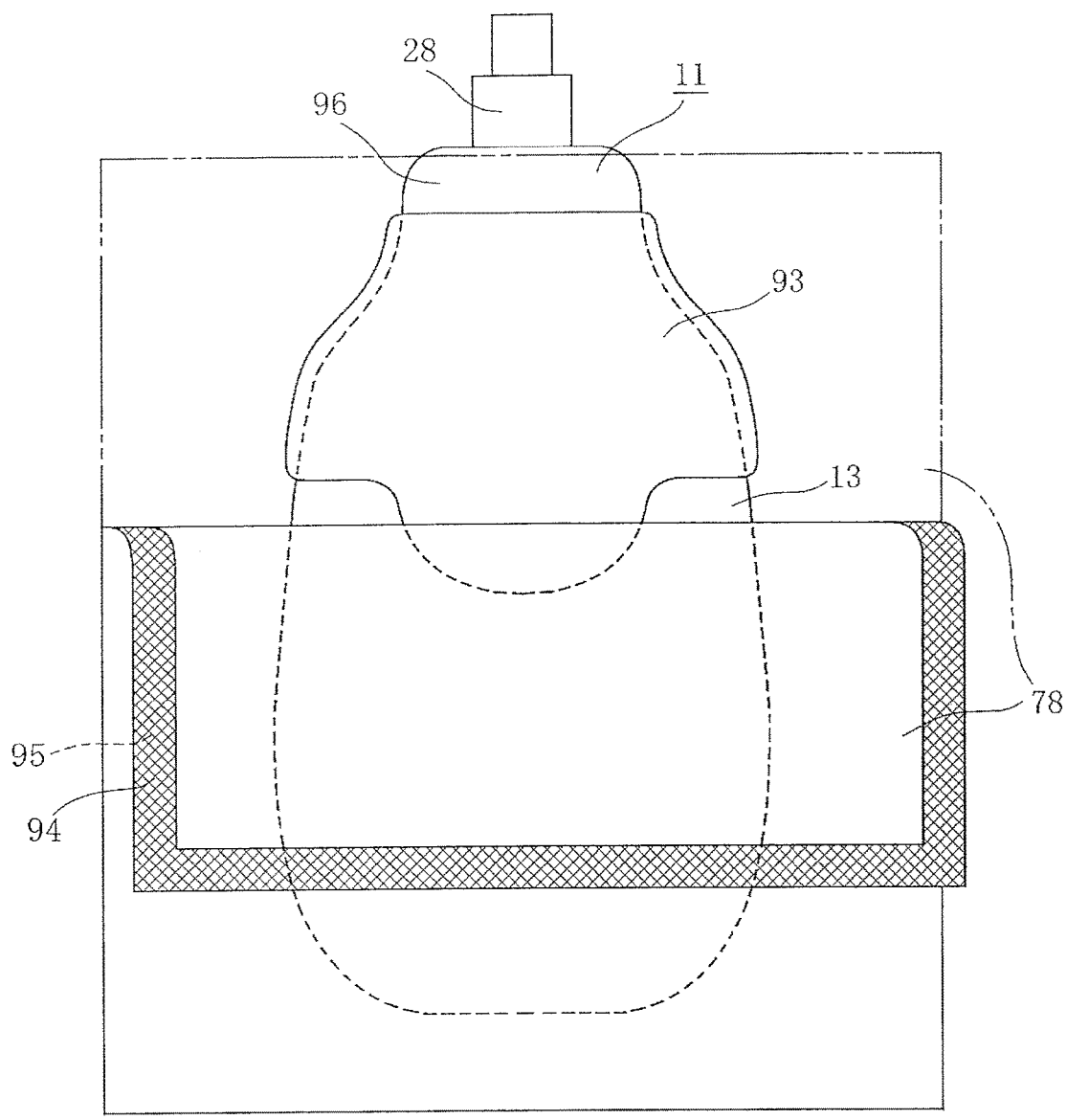
FIG. 16 is a base view showing other case of embodiment in a condition that the bed-sore preventive member is mounted as the bottom surface of the back cover portion and a part of the bilateral surfaces continuing from said bottom surface are covered.
Figure 17:
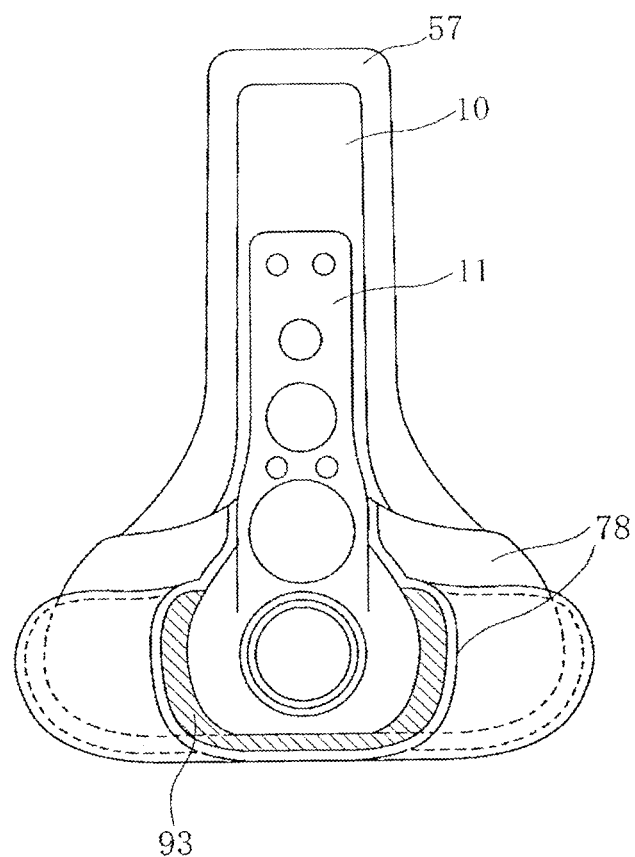
FIG. 17 is a back view with partial missing seen from the side surface of a part of the back cover portion in FIG. 16.
Figure 18:
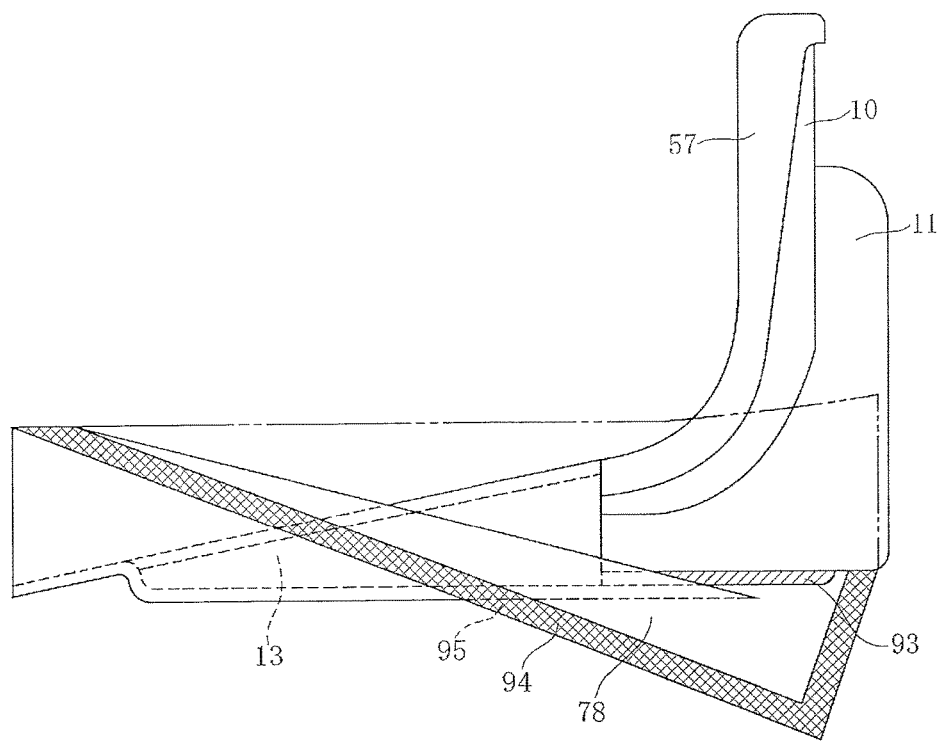
FIG. 18 is a side view with partial missing seen from the side surface of a part of the back cover in FIG. 16.
Figure 19:
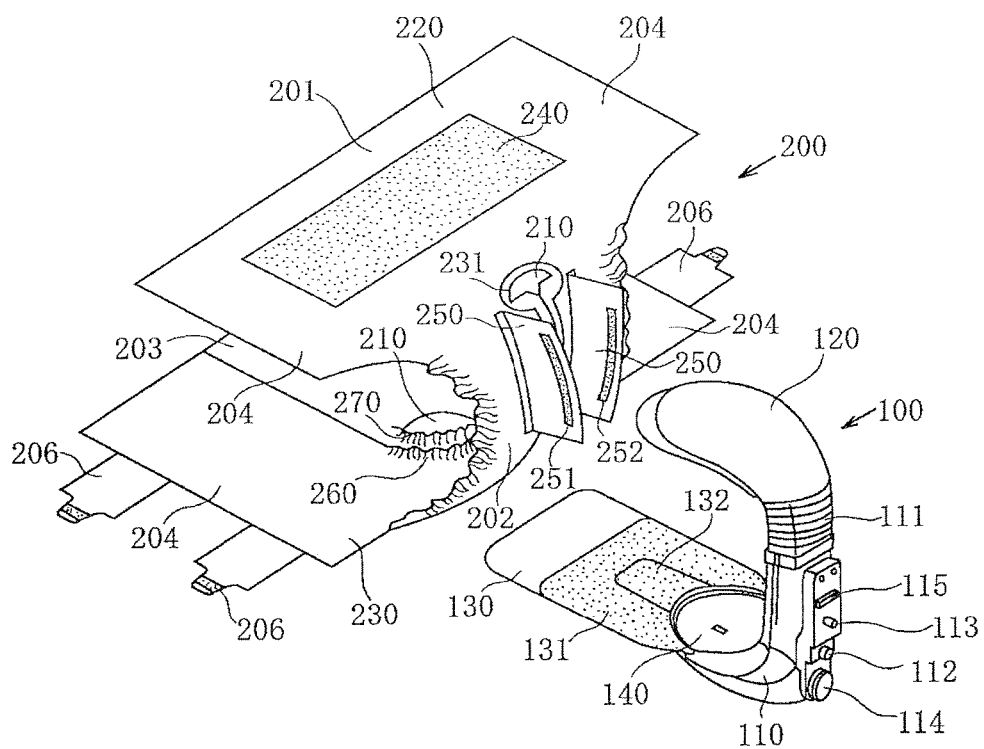
FIG. 19 is a diagrammatic perspective view of conventional wearable toilet seat and diaper.

Besides the first, second and third bed-sore preventive members 57, 58, and 59, as shown in FIGS. 16, 17, and 18, it is desirable to mount the fourth bed-sore preventive member 93 at the bottom surface of the back cover portion 11.

More specifically, the fourth bed-sore preventive member 93 is made from silicon rubber of 5~15 degree in hardness by JISA as the first bed-sore preventive member 57 and second bed-sore preventive member 58 are, and is fixed with adhesion in a manner that the bottom surface of the back cover portion 11 and a part of the surfaces of both the sides continuing from the bottom surface are wrapped. The fourth bed-sore preventive member 93 isn't mounted at the adhesive portion 96 to which the toilet seat cover cloth 78 at the bottom surface of said back cover portion 11 adheres. After the fourth bed-sore preventive member 93 is inserted to the plug-in gap 79 of the diaper 66, the peel-off sheet 94 is peeled off and the adhesive layer 95 bonds at the bottom surface and both the sides of the back cover portion 11 to prevent the leakage of urine and rinse solution from the sides of the main body 10. As shown in FIG. 14, mounting the fourth bed-sore preventive member 93 enables to surely prevent bed sore even in case of change in body position such as rolling over.

EXPLANATIONS OF LETTERS AND NUMERALS

10 . . . Main body of the toilet seat, 11 . . . . Back cover portion, 12 . . . Anterior cover portion, 13 . . . Hip receiving portion, 14 . . . Fecal receiving portion, 15 . . . Urine receiving portion, 16 . . . Femoral receiving portion, 17 . . . Rinse solution nozzle, 18 . . . Rinse solution nozzle, 19 . . . Fecal suction hole, 20 . . . Tenon hole, 21 . . . Assembly ligula, 22 . . . Assembly projection, 23 . . . Fecal sensor, 24 . . . Urine sensor, 25 . . . Wind-guide long hole, 26 . . . Tubular portion, 27 . . . Basal receiving portion, 28 . . . Backside receiving portion, 29 . . . . Basal airspace portion, 30 . . . Backside airspace portion, 31 . . . Side wall portion, 32 . . . Hose plug-in hole, 33 . . . Air-blasting pipe mounting hole, 34 . . . Rinse solution pipe mounting hole, 35 . . . Connector mounting hole, 36 . . . Assembly ligula, 37 . . . Assembly projection, 38 . . . Nozzle escape concave portion, 39 . . . . Cylinder cowling, 40 . . . Wind-guide fin, 41 . . . Tenon, 42 . . . . Screw hole, 43 . . . Upward spray nozzle, 44 . . . Horizontal spray nozzle, 45 . . . Water conduit pipe, 46 . . . Air blasting route, 47 . . . Wind guide groove member, 48 . . . Wind-guide groove portion, 49 . . . Air-blasting pipe connecting member, 50 Water pipe connecting member, 51 . . . Connector, 52 . . . Excretory-substance suction hose, 53 . . . Air supply pipe, 54 . . . Water pipe, 55 . . . Electric cord, 56 . . . Air-blasting pipe, 57 . . . First bed-sore preventive member, 58 . . . Second bed-sore preventive member, 59 . . . Third bed-sore preventive member, 60 . . . Sacral escape concave portion, 61 . . . Plug-in groove, 62 . . . Get-on concave portion, 63 . . . Basal portion, 64 . . . Screw hole, 65 . . . Screw, 66 . . . Diaper, 67 . . . Diaper main body, 67a . . . Waist contour wrapping portion, 67b . . . Abdominal contour wrapping portion, 67c Crotch contour wrapping portion, 70 Gather, 71 . . . Fixing member, 72 . . . Face fastener, 73 . . . Leakage preventive wimple, 74 . . . Excretion hole, 75 . . . Adhesive member, 76 . . . Cushion member, 77 . . . Gather tape, 78 . . . Toilet-seat cover cloth, 79 . . . Plug-in gap, 80 . . . Male sexual organ retentive portion, 81 . . . Gap retentive portion, 82 . . . Cap retentive tape, 83 . . . Joint band, 84 . . . Circuit board, 85 . . . Anus, 86 . . . Feces, 87 . . . Bump, 88 . . . Inner wall portion, 89 . . . Plunger helix, 90 . . . Assembly ligula, 91 . . . Marginal region, 92 . . . . Marginal region, 93 . . . Fourth bed-sore preventive member, 94 . . . Peel-off sheet, 95 . . . Adhesive layer, 96 . . . Adhesive portion

The invention claimed is:

1. A wearable toilet seat comprising:
   a main body of the toilet seat equipping a nearly horizontal patelliform defecated fecal receiving portion and a nearly vertical caniliform urine receiving portion,
   a back cover portion fitted with a back side of the main body of the toilet seat from an underside, and
   a hip receiving portion mounted at an anterior end of said main body of the toilet seat,
   in which bed-sore preventive members are mounted at a marginal region of said defecated fecal receiving portion and said urine receiving portion and at an upper surface of said hip receiving portion,
   wherein the back cover portion is fitted from the back side and a bottom surface in the main body of the toilet seat,
   wherein a wind-guide long hole opening upward is set at the marginal region of the defecated fecal receiving portion in said main body of the toilet seat, an anterior cover portion is covered on the wind-guide long hole as having a gap, a cylinder cowling is set along a lining of an inner wall of the defecated fecal receiving portion of the anterior cover portion as having a gap, multiple wind guide fins are arranged at a gap with the inner wall of said cylinder cowling with specified intervals and angles, and regions among said multiple wind guide fins are made air blasting routes.

2. The wearable toilet seat according to claim 1, wherein the intervals and angles are formed in a manner that a wind volume at nearly center of the defecated fecal receiving portion becomes larger than those at two sides of the defecated fecal receiving portion.

3. The wearable toilet seat according to claim 1, wherein the intervals and angles of the wind guide fins are formed in a manner that wind volumes at two sides of the defecated fecal receiving portion become larger than that at the center of the defecated fecal receiving portion.

* * * * *